United States Patent
Fuchs et al.

[11] 3,931,186
[45] Jan. 6, 1976

[54] PROCESS FOR PREPARING NAPHTHOLYENE ARYLIMIDAZOL-PERI-DICARBOXYLIC ACID IMIDES

[75] Inventors: Otto Fuchs, Frankfurt am Main; Adolf Kroh, Munster, Oberlahnkreis, both of Germany

[73] Assignee: Hoechst Aktiengesellschaft, Frankfurt am Main, Germany

[22] Filed: Sept. 18, 1973

[21] Appl. No.: 398,559

[30] Foreign Application Priority Data
Sept. 20, 1972 Germany............................ 2246110

[52] U.S. Cl. ........ 260/282; 260/281 N; 260/281 A; 8/1 B; 8/179
[51] Int. Cl.² .................................... C07D 471/16
[58] Field of Search ................................. 260/282

[56] References Cited
FOREIGN PATENTS OR APPLICATIONS
551,183    5/1932    Germany ........................... 260/282

Primary Examiner—Nicholas S. Rizzo
Assistant Examiner—Mark L. Berch
Attorney, Agent, or Firm—Curtis, Morris & Safford

[57] ABSTRACT
Process for preparing naphthoylene-arylimidazo-peri-dicarboxylic acid-imide-compounds of the formula

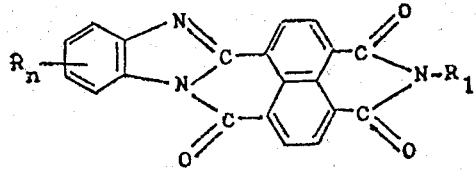

wherein $R_1$ is hydrogen, hydroxy or amino, phenyl, alkyl having 1 to 8 carbon atoms, hydroxyalkyl, alkoxyalkyl, amino-alkyl, mono- or dialkylaminoalkyl, hydroxyalkoxyalkyl, alkoxyalkoxyalkyl, carbalkoxyalkyl, carboxylalkyl or phenyl-alkyl having each 1 to 6, preferably 1 to 4 carbon atoms in the alkyl or alkoxy portion and R is hydrogen or halogen, alkyl, alkoxy, carbalkoxy having each 1 to 4 carbon atoms, nitro, cyano, carbonamido, mono- or dialkylcarbonamido or sulfonamido, mono- or dialkylsulfonamido and n represents the integers 1 to 3, in which process naphthalimide-4,5-dicarboxylic acids of the general formula

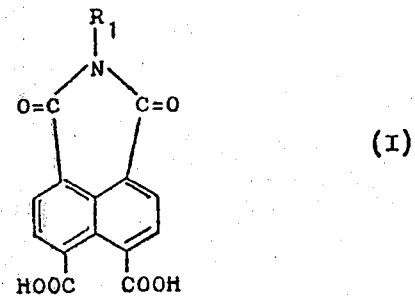

(I)

or the anhydride thereof are condensed in an aqueous medium with a diamine of the general formula

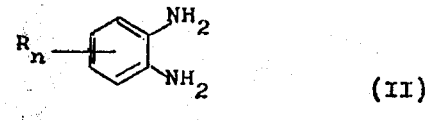

(II)

at temperatures of from 80° to 160°C. $R_1$, R and $n$ having the above meanings.

1 Claim, No Drawings

PROCESS FOR PREPARING NAPHTHOLYENE ARYLIMIDAZOL-PERI-DICARBOXYLIC ACID IMIDES

This new process provides a method to get the dyestuffs of the naphthylene-arylimidazol-peri-dicarboxylic-acid-imide series in an outstanding pure form.

Dyestuffs belonging to the naphthylene-arylimidazol-peri-dicarboxylic acid imide series are known, for example, from German Pat. Nos. 1,049,821 and 1,268,581 and from German Offenlegungsschrift No. 1,719,090. Individually or as mixture they are very suitable for dyeing fibres from polyester, polyacrylonitrile and cellulose acetate, yielding brilliant greenish-yellow to orange dyeings with excellent fastness properties.

According to the processes hitherto described these known dyestuffs or the mixtures thereof are only prepared by condensation of naphthoylene-arylimidazol-peri-dicarboxylic acids or the anhydrides thereof with monoamines in water or organic solvents at elevated temperatures.

The naphthoylene-armylimidazol-peri-dicarboxylic acid or the anhydrides thereof required for this method of preparation are prepared advantageously according to a process described in German Pat. No. 1,005,969, according to which the mono-sodium salt of the naphthanlene-1,4,5,8-tetra-carboxylic acid is reacted in 20 to 40 times the amount of water and in the presence of big amounts of buffer substances with ortho-phenylene-diamine at 70°to 90°C.

The mono-sodium salt formed during condensation is difficultly soluble in the salt solution and is precipitated. Depending on the basicity of the o-diamine used it contains up to 15% of a red dyestuff as by-product, which has been formed by condensation of the two peri-dicarboxylic acid groups with the o-diamine. However, a reduction of the salt concentration leads to even bigger amounts of the red by-product and the condensation of the naphthalene-tetracarboxylic acid is no longer quantitative. Therefore, for further processing, an intermediate isolation and purification by dissolving in alkali and reprecipitation is absolutely required to separate the red by-product.

The present invention relates to a novel process for preparing naphthoylene-arylimidazol-peri-dicarboxylic acid imide compounds of the fromula

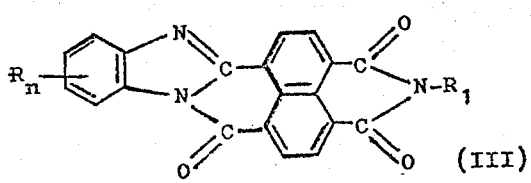

(III)

wherein $R_1$ is hydrogen, hydroxy or amino, phenyl, alkyl having 1 to 8 carbon atoms, hydroxyalkyl, alkoxyalkyl, amino-alkyl, mono- or dialkylaminoalkyl, hydroxyalkoxyalkyl, alkoxyalkoxyalkyl, carbalkoxyalkyl, carboxylalkyl or phenylalkyl having each 1 to 6, preferably 1 to 4 carbon atoms in the alkyl or alkozy portion and R is hydrogen or halogen, alkyl, alkoxy, carbalkoxy having each 1 to 4 carbon atoms, nitro, cyano, carbonamido, mono- or dialkylcarbonamido or sulfonamido, mono- or dialkylsulfonamido and n represents the integers 1 to 3, in which process naphthalimide-4,5-dicarboxylic acids of the general formula

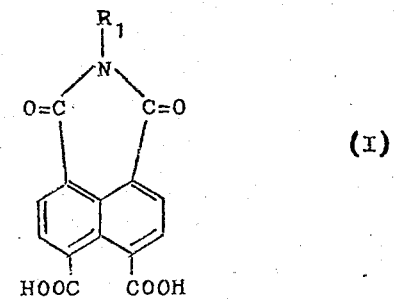

(I)

or the anahydride thereof are condensed in an aqueous medium with a diamine of the general formula

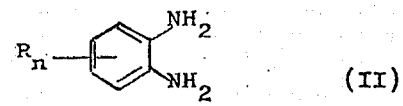

(II)

at temperatures of from 80°to 160°C, $R_1$, R and n having the above meanings.

The preparation of the naphthalimide-4,5-dicarboxylic acids is advantageously carried out by suspending 1 mol of the 1,4,5,8-naphthaline-tetracarboxylic acid, generally available as a semi-anhydride, in 12 to 20 times the amount of water, heating the suspension to 60°–95°C and dissolving the naphthalene-tetracarboxylic acid with the 2 to 6-molar amount of sodium or potassium hydroxide solution. Then the pH-value was adjusted to about 5.0 –5.6 with phosphoric acid or acetic acid, and the amount of the amine calculated accordingly is added in a slight excess of up to 10 %, the pH-value being adjusted to 5.2 –7.5. Then the condensation reaction is carried out at an elevated temperature, either under reflux or in a closed reaction vessel at a temperature of preferably 106°to 135°C during 2 to 6 hours, preferably 3 to 5 hours. During this period the naphthalene-tetracarboxylic acid is reacted quantitatively with the amine. Particularly when using aliphatic amines, the condensation product obtained as alkali salt, is easily soluble in the reaction solution in the heat and can be easily freed by simple filtration from the corresponding naphthalene-tetracarboxylic acid diimide undissolved and formed simultaneously in a few portions from the corresponding naphthalene-tetracarboxylic acid diimide undissolved and formed simultaneously in a few portions. By acidifying the clarified solution with mineral acid, fultering the deposit formed and subsequently drying, the corresponding naphthalimide-4,5-di-carboxylic acids are obtained in a pure form and in very high to practically quantitative yields. Instead of one individual amine a mixture of different amines can also be used for condensation.

The free naphthalimide-dicarboxylic acids can be converted in known manner into the corresponding anhydrides, for example by heating in a high-boiling solvent, such as trichlorobenzene or α-chloro-naphthalene, while distilling off the water set free in the heat. With the rapid vatting in alkaline sodium dithionite solutions the imide anhydrides according to the invention show a characteristic pure blue vat color.

In the cases in which, during condensation, less well-soluble alkali salts are formed, which are no longer completely soluble in the reaction solution in the heat, the reaction solution is acidified with mineral acid and the amide-dicarboxylic acids precipitated are isolated. To separate from the unsoluble diimide which has also formed, the moist crude product is suspended in water, the imide-dicarboxylic acid is dissolved in the heat by addition of sodium carbonate solution and the diimide is separated by filtration. In the same way as described above the imide-dicarboxylic acid is isolated. In this working-up care must be taken that the pH-value of the solution is not considerably superior to 8.0 after addition of the soda solution, since the naphthalimide-4,5-dicarboxylic acids are saponified very easily to give the naphthalene-tetra-carboxylic acid. This fact is unusual since most of the naphthalimides are very resistant to alkalis in the heat and can be saponified only with difficulty.

Amines which are used for the condensation with naphthalene-tetra-carboxylic acid are for example: ammonia, hydroxyl amine, hydrazine, straight-chained and branched alkyl amines such as methyl-, ethyl-, proply-, butyl-, hexylamine, isopropyl-, isobuty-, 2-ethyl-hexylamine; straight-chained and branched alkyl amines substituted by hydroxy and/or alkoxy groups, such as amino-ethanol, aminopropanol, 2-amino-i-butanol, methoxy-ethylamine, methoxypropylamine, ethoxypropylamine, isopropoxy-propylamine, n-butoxy-propylamine, 3- ($\Omega$-ethoxy)-ethoxy-propylamine, 3-($\Omega$-hydroxy)-ethoxy-propylamine; alkylamines substituted by caroboxyl groups, such as aminoacetic acid, 3-aminopropionic acid, 4-amino-butyric acid as well as the alkyl esters thereof; alkyl amines substituted by phenyl such as benzyl amine or phenyl-ethyl-amine.

Among these amines the aliphatic amines, especially the alkyl-, hydroxy-alkyl- and alkoxyalkyl-amines, are especially important, since the naphthalimide-4,5-dicarboxylic acids prepared with these amines provide, after a condensation with aromatic diamines, valuable dyestuffs of the naphthoylenearylimidazol-peri-dicarboxylic acid-imide series.

The preparation of these dyestuffs is advantageously effected on the basis of the suspension of the naphthalimide4,5-dicarboxylic acids, as it is obtained in the process described above. The equivalent amount of a phenylene-diamine of the formula (II) is added directly to this suspension and condensation is carried out at 80°C to 160°C, if desired in an autoclave. The reaction time is between 1 and 5 hours, mostly 2 to 3 hours. The dyestuff obtained is isolated in usual manner.

Of course, it is also possible to use the suspension of the naphthalimide-4,5-dicarboxylic acid not directly, but to isolate first this intermediate product and to purify it, if desired, by dissolution in alkali. The new process is also suitable for preparing the naphthoylene-arylimidazol-peri-dicarboxylic acid-imides of the general formula I, in which $R_1$ represents a substituted phenyl ring. However, up to now, such compounds have not been used as dyestuffs on account of their coloristical disadvantages.

The N-alkyl-naphthalimide-4,5-dicarboxylic acids especially suitable for the preparation of the naphthoylene-arylimidazolperi-dicarboxylic acid-imide-dyestuffs are mostly well-soluble in water in the form of their alkali salts. Therefore, they can be separated, very easily by filtration from the diimide which has possibly formed. After acidifying this filtrate the suspension obtained can be condensed directly with the phenylene-diamine to give the dyestuff. The dyestuffs prepared by this way are particularly pure. This purity can be obtained only if the naphthalimide-4,5-dicarboxylic acids are completely free from the starting material, since the condensation of napthaline-tetracarboxylic acid having on both sides o-diamines leads to red vat dyestuffs, which are not suitable for dyeing polyester material and are detrimental to the shade desired.

The new process has the further advantage that by the reduction of the liquid volume and of the reaction times the double amount can be prepared in the same period.

Since in camparision to processes hitherto known from German Pat. No. 1,005,969 an intermediate isolation and alkaline dissolution is no longer necessary, it is possible to prepare a considerably bigger amount in a less complicated apparatus and with a reduced expenditure of work. Furthermore, the yield of dyestuff is nearly quantitative whereas in the cases in which, strongly alkaline o-diamines are used, yields of only 80 to 85 % are obtained according to the known process. Another fact is that in the new process the amounts of waste water are considerably smaller and contain less salt.

The following Examples illustrate the invention. Parts and percentages are by weight unless stated otherwise.

EXAMPLE 1

20 Parts of naphthalene-1,4,5,8-tetracarboxylic acid in the form of the semi-anhydride were dissolved in 300 parts of water with 34 parts of sodium hydroxide solution (33 %) at 70°C. By addition of 10.6 parts of phosphoric acid (80 %) and 6.6 parts of 3-methoxy-n-propylamine, a pH-value of 5.8 to 6.1 was adjusted, and the mixture was stirred for 3 hours at 130°C in a closed vessel. After cooling to 60°–90°C it was filtered from the small amount of by-product formed, the filtrate was adjusted to pH 2.8–3.2 with 15 parts of glacial acetic acid and 18 parts of hydrochloric acid (36 %) and after addition of 10 parts of 3,4-diamino-benzonitrile, the mixture was stirred for 5 hours in a closed vessel at 150°C. At 90°C the condensation product was suction-filtered, washed free from salt and dried.

The greenish-yellow dyestuff obtained in a nearly quantitative yield was completely free from naphthalene-tetracarboxylic acid condensed on both sides with 3,4-diamino-benzo-nitrile (orange red dyestuff) and dyed polyester fibres - after a corresponding preparation - in a brilliant greenish-yellow shade.

EXAMPLE 2

93.8 Parts of naphthalene-tetracarboxylic acid anhydride were dissolved in 1500 parts of water at 9520 C by addition of 170 parts of sodium hydroxide solution (33 %), and mixed with 53 parts of phosphoric acid (80 %). After addition of 13.2 parts of 3-methoxy-n-propylamine and 31.25 parts of 3-butoxy-n-propylamine a pH-value of 5.8 to 6.1 was adjusted. Then the mixture was stirred for 3 hours at 130°C. Then it was filtered from a small amount of diimide formed, adjusted to a Congo acidic range with 112 parts of hydrochloric acid (36 %) and stirred for 4 hours at 95C after addition of 52 parts of 4-chloro1,2-diaminobenzene. The dyestuff mixture formed in a nearly quantitative yield was completely free from naphthalene-tetra-carboxylic acid condensed on both sides with 4-chloro-1,2-diaminobenzene (red dyestuff). It was suction-filtered with water, washed free from salt and dried. After a corresponding fine division the dyestuff mixture dyed polyester fibres in a brilliant yellow shade.

EXAMPLE 3

50 Parts of naphthalene-1,4,5,8-tetracarboxylic acid in the form of the semi-anhydride were suspended in 750 parts of water and dissolved at 70°C –80°C with 98 parts of KOH (40 %). By addition of 25 parts of phosphoric acid (85 %) and 16.5 parts of 3-methoxy-n-propylamine, a pH-value of 5.8 –6.1 was adjusted and the mixture was stirred at 130°C for 5 hours. At 90°C, the pH-value was adjusted to a Congo acidic range with hydrochloric acid, the mixture was stirred for half an hour at 80°C and the N-(3'-methoxy-n-propyl)-naphthalimide-4,5-dicarboxylic acid contaminated by small amounts of naphthalene-tetracarboxylic acid-dimide was suction-filtered and washed free from salt. The moist press-cake was suspended at 70°C in 700 parts of water and dissolved by addition of a 10 % soda solution at pH 7.0 to 7.5, then the mixture was filtered from the diimide and the filtrate was adjusted to pH 2.5 –2.8 with 15 parts of acetic acid and hydrochloric acid (36 %). After addition of 23 parts of 4-methyl-1,2-diaminobenzene the mixture was stirred for 5 hours at 100° C, then suction-filtered, washed free from salt with water and dried. The orange dyestuff obtained in a nearly quantitative yield was completely free from naphthalenetetracarboxylic acid condensed on both sides with 4-methyl-1,2diaminobenzene and dyed polyester fibres - after a corresponding preparation- in a brilliant orange dyestuff.

EXAMPLE 4

100 Parts of naphthalene-1,4,5,8-tetracarboxylic acid in the form of the semi-anhydride were dissolved in 1500 parts of water at 50°C with 170 parts of sodium hydroxide solution (33 %), stirred for 10 minutes, mixed with 48 parts of glacial acetic acid (pH = 5.3) and after addition of 33 parts of 3-methoxy-propylamine (pH = 5.7 - 5.9) stirred for 5 hours at 130°c. Then the mixture was filtered at 79°–90°C from the small amount of diimide formed and adjusted to the Congo acidic range with hydrochloric acid. After addition of 25.7 parts of 3,5-dimethyl-1,2-diamino-benzene and 26 parts of 4-chloro-1,2-diaminobenzene the whole was stirred for 4 –5 hours at 95°C. The reddishyellow dyestuff mixture obtained was suction-filtered, washed free from salt and dried. It dyed polyester material after a previous fine division in a brilliant reddish yellow shade.

EXAMPLE 5

100 Parts of naphthalene-1,4,5,8-tetracarboxylic acid in the form of the semi-anhydride thereof were suspended in 1500 parts of water and dissolved at 95°C by addition of 106.8 parts of NaOH (33 %), then 16 parts of phosphoric acid (85 %) and 33 parts of 3-methoxy-propylamine were added and the whole was stirred for 4 hours at 125°C. It was separated from a small amount of the naphthalene-tetracarboxylic acid-diimide formed, the filtrate was adjusted to pH 1.5 with hydrochloric acid and after addition of 42 parts of 1,2-diaminobenzene, stirred for 5 hours at 95°–100°C. The yellow dyestuff formed was isolated, washed free from salt and dried. In a finely divided form it dyed polyester in a brilliant yellow shade.

EXAMPLE 6

50 Parts of naphthalene-1,4,5,8-tetracarboxylic acid in the form of the semi-anhydride thereof were suspended in 750 parts of water and dissolved at 80°C by addition of 82 parts of sodium hydroxide solution. After 10 minutes 21 parts of phosphoric acid (85 %) and 37 parts of ammonia were added and the whole was stirred for 4 hours at 130°C and the naphthalimide-4,5-dicarboxylic acid contaminated by small amounts of naphthalene-tetracarboxylic acid diimide was isolated.

The press-cake was suspended in 2 liters of water, the suspension was heated to 80°C and dissolved at pH 7 to 7.5 by addition of a 10 % soda solution, the diimide formed was separated by filtration and adjusted to pH 2.8 with hydrochloricacid (36 %) of 30 parts of glacial acetic acid. Then 26 parts of 4-chloro-1,2-diaminobenzene were added and heated for 4 hours to 130°C. The yellow condensation product was suction-filtered at 90°C, washed free from salt and dried. In a finely divided form it was suitable for dyeing polyester fabrics according to the thermosol process.

EXAMPLE 7

50 Parts of naphthalene-1,4,5,8-tetracarboxylic acid in the form of the semi-anhydride thereof were suspended in 750 parts of water and dissolved at 80°C by addition of 82 parts of sodium hydroxide solution (33 %). Stirring was continued for 10 minutes and after addition of 21 parts of a 85 % phosphoric acid and 15 parts of a 40 % methylamine solution, the mixture was stirred for 5 hours in a closed vessel at 135°C. At 90°C it was filtered from the small amount of diimide formed, the pH- value was adjusted to 2.8 –3.0 with 46 parts of hydrochloric acid (36 %) and 37 parts of glacial acetic acid and stirred for 30 minutes at 80°–90°C. Then 31.5 parts of 3.4-diamino-benzoic acid methyl ester were added and stirred for 5 hours at 130°–135°C.

The dyestuff formed was suction-filtered at 80°C, washed free from salt and dried.

It dyed polyester fibres - after a corresponding preparation - in a clear greenish yellow shade.

The dyestuffs of the general formula

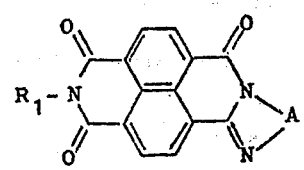

listed in the following Examples were obtained according to the method indicated in Example 7.

-continued

| Example | R | A | Shade of the polyester dyeing |
|---------|---|---|------------------------------|
| 8 | CH₂—CH₂—CH₂—OH | 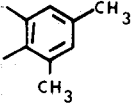 | orange |
| 9 | —(CH₂)₅—CH₃ | 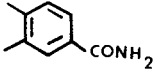 | yellow |
| 10 | —CH(CH₃)CH₃ | 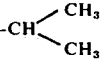 | yellow |
| 11 | (CH₂)₃—O—CH₂—CH₂—OCH₂—CH₃ | 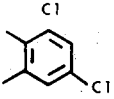 | yellow |
| 12 | —CH₂—CH₂—CH₂—COOH |  | orange |
| 13 | —CH₂—COOC₂H₅ |  | orange |
| 14 | —(CH₂)₃O—C₂H₅ } in the molar ratio | 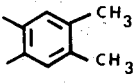 | greenish yellow |
| 15 | —(CH₂)₃—CH₃  1 : 1<br>—CH₃ } in the molar ratio<br>—(CH₂)₃—O—(CH₂)₂—OC₂H₅  4 : 6 | 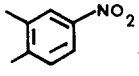 | yellow |
| 16 | —(CH₂)₃—O—CH₂—CH₂—OH |  | orange |
| 17 | —(CH₂)₃—OCH₃ | 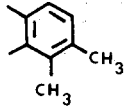 | greenish yellow |

The dyestuffs listed in the following Examples were obtained according to the process indicated in Example 6

| 18 | —OH | 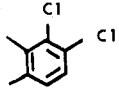 | yellow |
| 19 | —N—H₂ |  | yellow |
| 20 | —CH₂— | 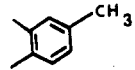 | orange |

EXAMPLE 21

50 g of naphthalene-tetracarboxylic acid in the form of the semi-anhydride thereof were suspended in 750 g of water and dissolved at 70°–80°C with 85 g of sodium hydroxide solution. After addition of 25 g of phosphoric acid (85 %) and 21.5 g of 2-(N,N-diethylamino)-ethylamine, a pH-value of 7.0 –7.2 was adjusted. Then the whole was stirred for 5 hours at 130°C, filtered at 90°C from the small amount of diimide, adjusted to pH 2.0 –2.2 with hydrochloric acid and, after addition of 20.4 g of o-phenylene-diamine, stirred for 4 hours at 90°–98°C. Then the pH-value was adjusted to 7 with sodium hydroxide solution, the dyestuff formed was suction-filtered, washed free from salt with water and dried.

The dyestuff obtained in a nearly quantitative yield was completely free from tetra-acid condensed on both sides with o-phenylene-diamine, and in the form of the quaternary ammonium salt it dyed polyacrylonitrile in a yellow shade.

EXAMPLE 22

200 g of naphthalene-1,4,5,8-tetracarboxylic acid in the form of the semi-anhydride thereof were dissolved in 3000 ml of water and dissolved at 80°C with 340 g of sodium hydroxide solution (33 %). After 10 minutes the pH -value was adjusted to 5.1 –5.3 with 100 g of phosphoric acid (85 %) and after addition of 70 g of phosphoric acid (85 %) and after addition of 70 g of aniline, stirred for 4 to 5 hours at 130°C. The alkali salt formed of the N-phenyl-naphthalimide-4,5,-dicarboxylic acid was wholly dissolved in the heat and the naphthalene1,4,5,8-tetracarboxylic acid had quantitatively reacted. At 90°–95°C the mixture was separted from a small amount of naphthalene-1,4,5,8-tetracarboxylic acid-diphenyl-imide formed, the filtrate was adjusted to pH 1.5 –2 with hydrochloric acid and stirred for half an hour 80°C. The precipitated N-phenyl-naphthalimide-4,5-dicarboxylic acid was suction-filtered in the cold, washed free from salt with water and dried.

Yield: 94.3 % of the theory
Melting point of the anhydride: 318°C

EXAMPLE 23

50 g of naphthalene-1,4,5,8-tetracarboxylic acid-semianhydride were suspended in 750 ml of water and dissolved at 80°C with 85 g of sodium hydroxide solution (33 %). After 10 minutes the pH-value was adjusted to 5.2 with 25 g of phosphoric acid (85 %) and after addition of 18.9 g of N,N-dimethyl-1,3-diaminopropane (pH 7.5 ) the mixture was stirred for 4 hours at 130°C. At 80°C it was filtered from a small amount of naphthalene-tetracarboxylic acid-diimide formed and the filtrate was adjusted to a strongly Congo acidic range with hydrochloric acid and stirred for half an hour at 80°C. The hydrochloric salt precipitated of the N-[3-(N', N'-dimethylamino)-propyl]-naphthalimide-4,5-dicarboxylic acid was suction-filtered cold, washed with ethyl alcohol and dried.

Yield: 91 % of the theory
Melting point of the product isolated: 298°C.

What is claimed is:

1. Process for preparing naphthoylene-arylimidazol-peri-dicarboxylic acid-imide-compounds of the formula

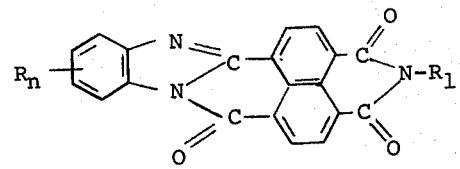

wherein $R_1$ is hydrogen, hydroxy or amino, phenyl, alkyl having 1 to 8 carbon atoms, hydroxyalkyl, alkoxyalkyl, amino-alkyl, mono- or dialkylaminoalkyl, hydroxyalkoxy-alkyl, alkoxyalkoxyalkyl, carbalkoxyalkyl, carboxylalkyl or phenyl-alkyl each having 1 to 6 carbon atoms in the alkyl or alkoxy portion and R is hydrogen or halogen, alkyl, alkoxy, carbalkoxy each having 1 to 4 carbon atoms, nitro, cyano, carbonamido, mono- or diloweralkylcarbonamide or sulfonamido, mono- or diloweralkylsulfonamido and n represents the integers 1 to 3, in which process naphthalimide-4,5-dicarboxylic acids of the formula

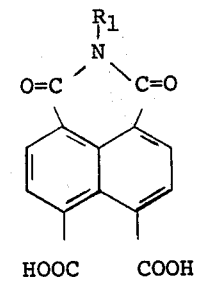

are condensed in a medium consisting essentially of water at a pH of from 1.5 to 4.0 with a diamine of the formula

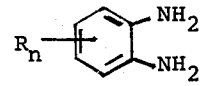

at temperatures of from 80°to 160°C, R, R and n having the above meanings.

* * * * *